(12) United States Patent
Guerrera et al.

(10) Patent No.: US 10,617,422 B2
(45) Date of Patent: Apr. 14, 2020

(54) SNAP RING CAM ACTUATOR RELEASE FOR A LOADING UNIT

(71) Applicant: Covidien LP, Mansfield, MA (US)

(72) Inventors: Joseph Guerrera, Watertown, CT (US); Anthony Sgroi, Jr., Wallingford, CT (US); Patrick Mozdzierz, Glastonbury, CT (US)

(73) Assignee: COVIDIEN LP, Mansfield, MA (US)

( * ) Notice: Subject to any disclaimer, the term of this patent is extended or adjusted under 35 U.S.C. 154(b) by 307 days.

(21) Appl. No.: 15/587,866

(22) Filed: May 5, 2017

(65) Prior Publication Data

US 2018/0317920 A1 Nov. 8, 2018

(51) Int. Cl.
*A61B 17/115* (2006.01)
*A61B 17/072* (2006.01)
*A61B 17/00* (2006.01)

(52) U.S. Cl.
CPC .... *A61B 17/1155* (2013.01); *A61B 17/07207* (2013.01); *A61B 2017/0046* (2013.01);
(Continued)

(58) Field of Classification Search
CPC . A61B 17/1155; A61B 17/064; A61B 17/068; A61B 17/07207;
(Continued)

(56) References Cited

U.S. PATENT DOCUMENTS

| 8,777,082 B2 | 7/2014 | Scirica |
| 2011/0174099 A1* | 7/2011 | Ross ................ A61B 17/072 |
| | | 74/89.32 |

(Continued)

FOREIGN PATENT DOCUMENTS

| EP | 2614784 A2 | 7/2013 |
| EP | 2623042 A2 | 8/2013 |

(Continued)

OTHER PUBLICATIONS

Extended European Search Report issued in corresponding European Application No. 18170920.5 dated Oct. 4, 2018.

*Primary Examiner* — Alexander M Valvis
*Assistant Examiner* — Himchan "Aiden" Song
(74) *Attorney, Agent, or Firm* — Carter, DeLuca & Farrell LLP

(57) ABSTRACT

A surgical instrument includes a shell assembly and an adapter. The shell assembly includes a shell housing, a plurality of staples, a staple pusher configured to eject the plurality of staples from the shell housing, a staple actuator configured to engage the staple pusher, a knife member, and a knife carrier supporting the knife member. The adapter includes a staple band operatively coupled to an actuation mechanism for axial displacement, a knife band at least partially received within the staple band, and a cam ring rotatably supported about the knife band. The staple band is configured to releasably engage the staple actuator. The knife band is operatively coupled with an actuation mechanism for axial displacement. The cam ring is rotatable between an engaged position in which the knife carrier engages the cam ring for concomitant axial displacement with the knife band and a disengaged position in which the knife carrier is disengaged from the cam ring.

15 Claims, 15 Drawing Sheets

(52) U.S. Cl.
CPC ............ *A61B 2017/00473* (2013.01); *A61B 2017/00477* (2013.01); *A61B 2017/07278* (2013.01); *A61B 2017/07285* (2013.01)

(58) Field of Classification Search
CPC .......... A61B 2017/00477; A61B 2017/07285; A61B 2017/0046; A61B 2017/00473; A61B 2017/07278
USPC .......................................... 227/175.1–182.1
See application file for complete search history.

(56) References Cited

U.S. PATENT DOCUMENTS

| | | |
|---|---|---|
| 2012/0253329 A1 | 10/2012 | Zemlok et al. |
| 2013/0181036 A1* | 7/2013 | Olson ............... A61B 17/1155 227/180.1 |
| 2013/0200131 A1* | 8/2013 | Racenet ............... A61B 17/072 227/180.1 |
| 2016/0000428 A1* | 1/2016 | Scirica ................... A61B 50/30 227/180.1 |
| 2016/0007999 A1* | 1/2016 | Latimer ................. A61B 90/30 606/219 |
| 2016/0022267 A1* | 1/2016 | Milliman ........... A61B 17/1155 227/181.1 |
| 2016/0106406 A1 | 4/2016 | Cabrera et al. |
| 2016/0157856 A1 | 6/2016 | Williams et al. |
| 2016/0192938 A1 | 7/2016 | Sgroi, Jr. |
| 2016/0192939 A1 | 7/2016 | Sgroi, Jr. et al. |
| 2016/0310141 A1 | 10/2016 | Penna et al. |
| 2017/0079660 A1 | 3/2017 | Sgroi |

FOREIGN PATENT DOCUMENTS

| | | |
|---|---|---|
| EP | 3085316 A1 | 10/2016 |
| WO | 2014139467 A1 | 9/2014 |

* cited by examiner

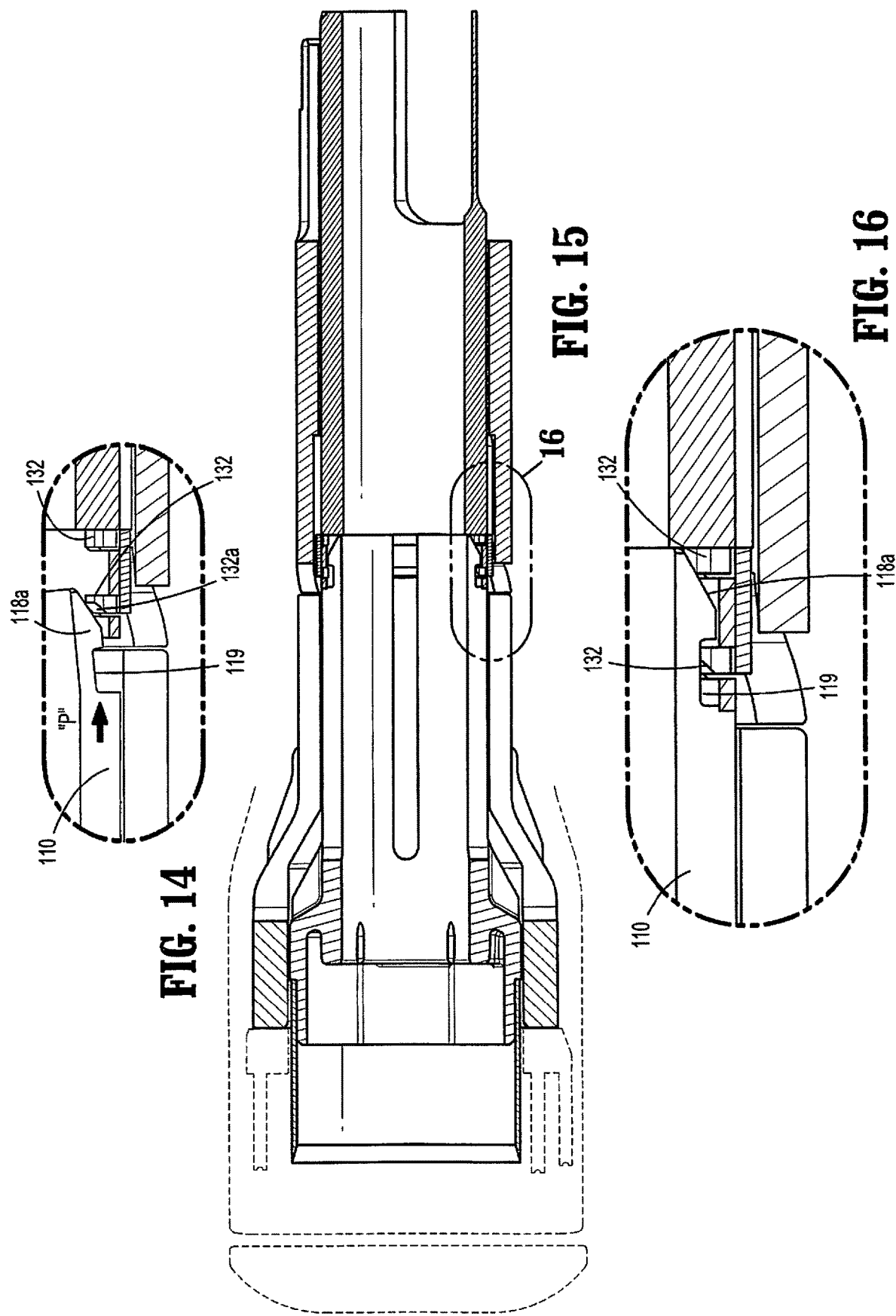

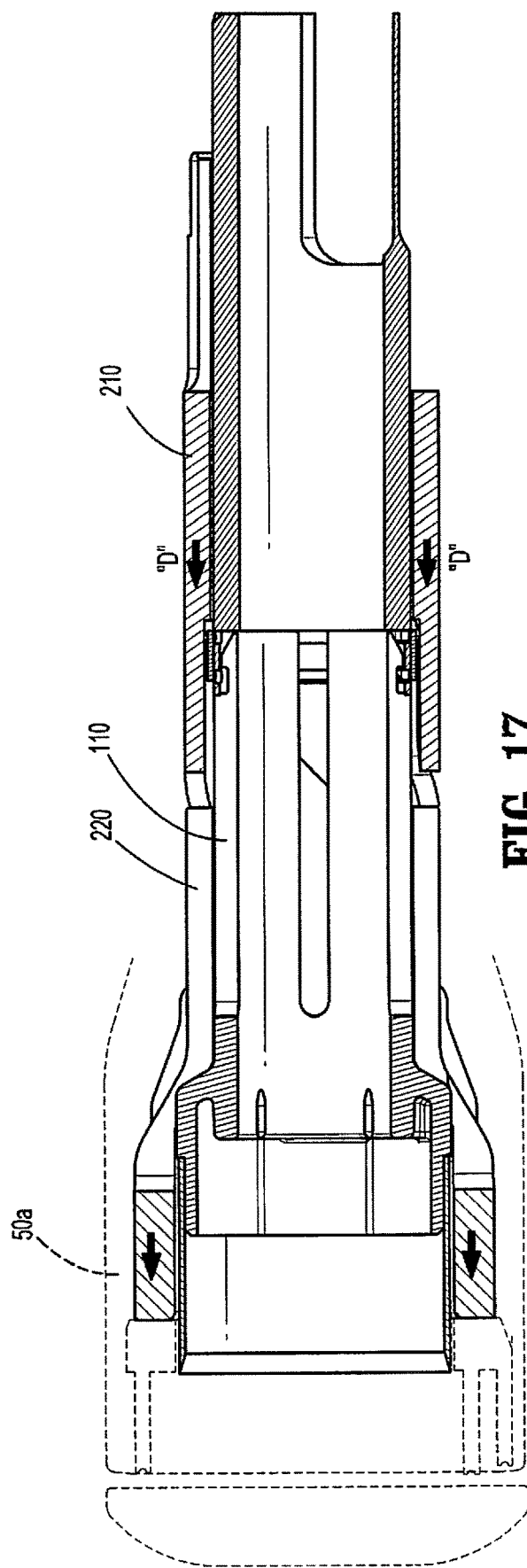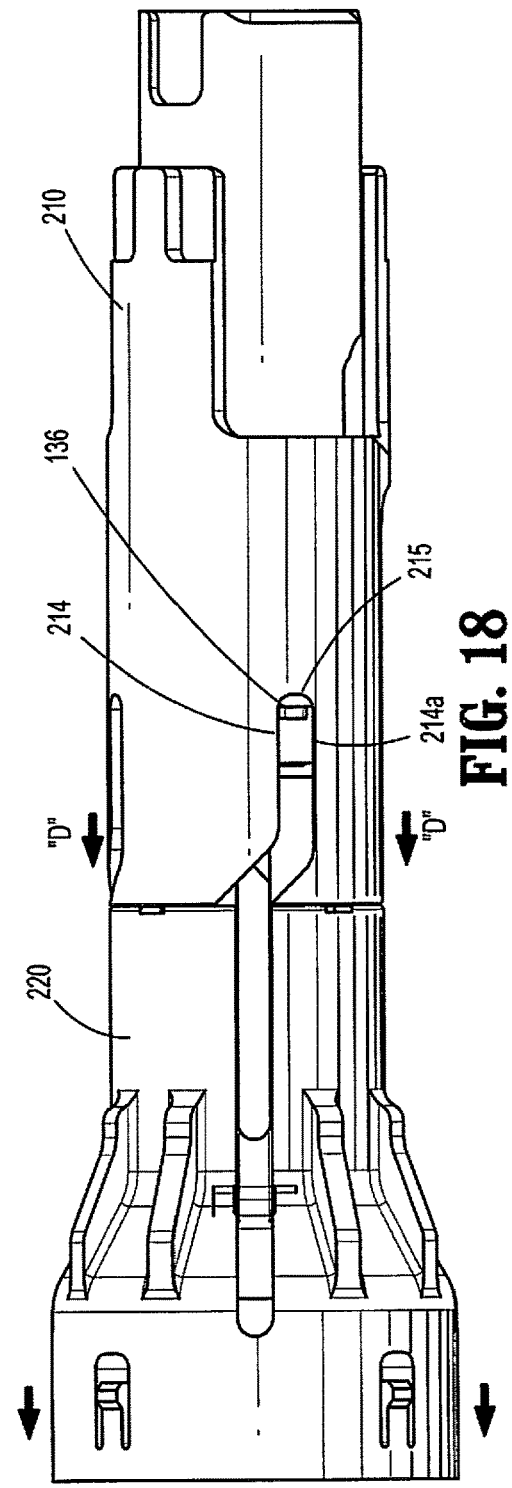

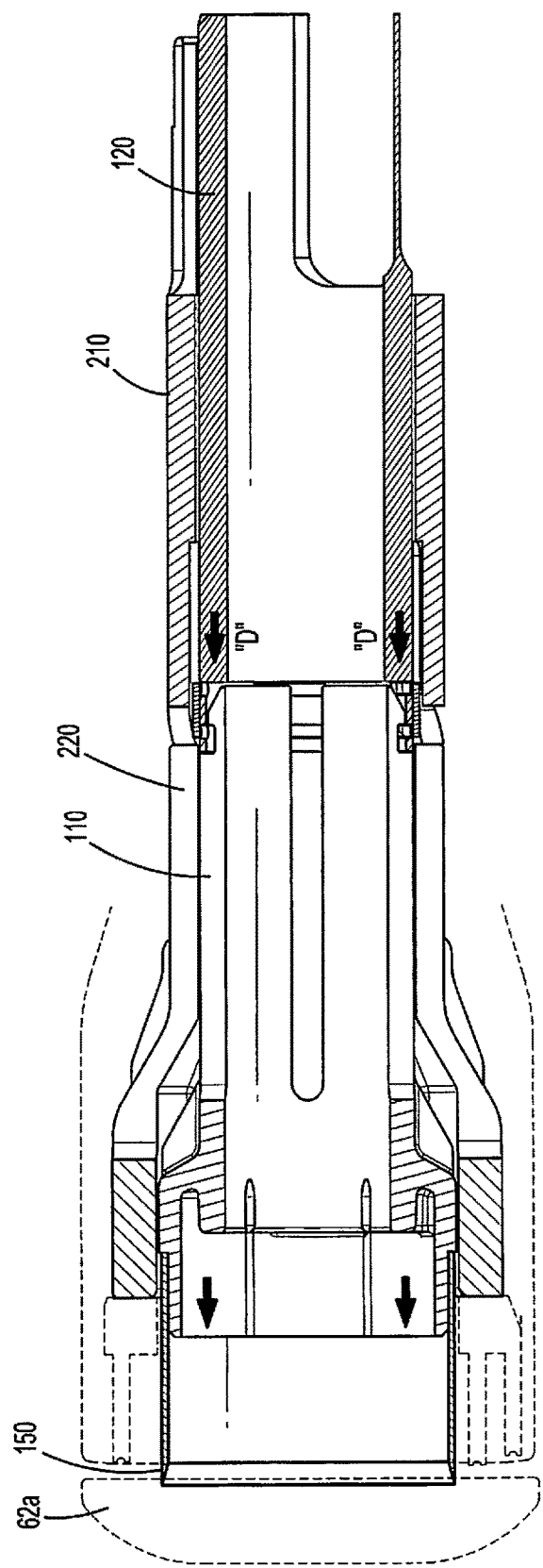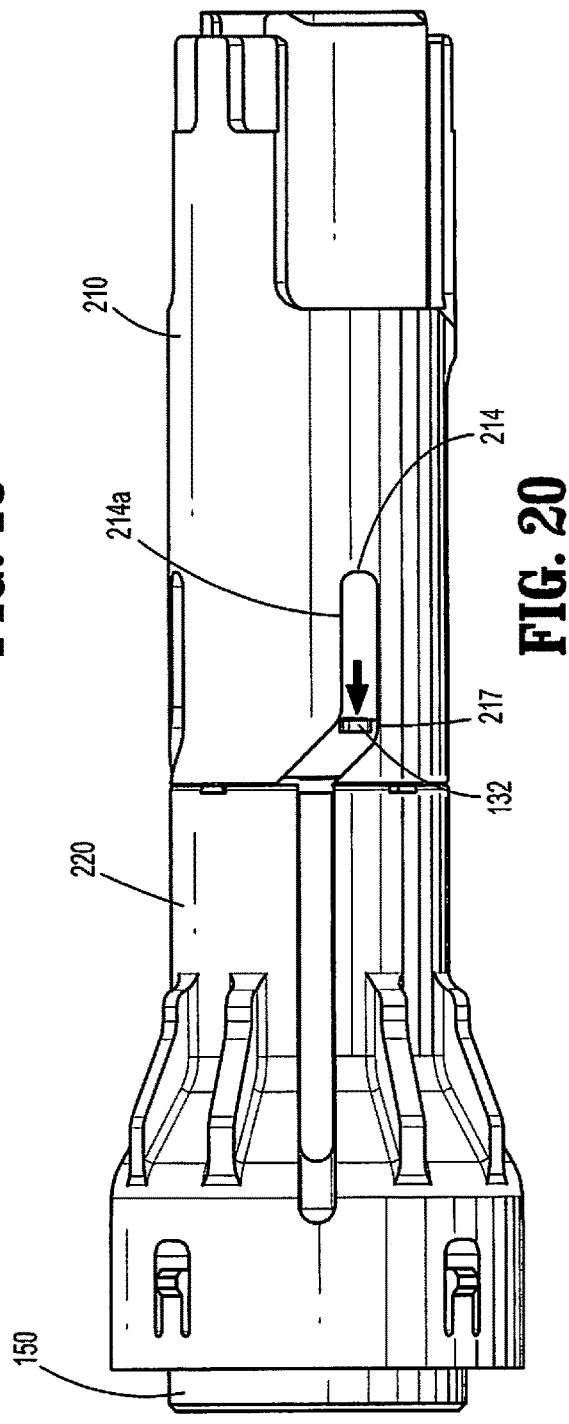

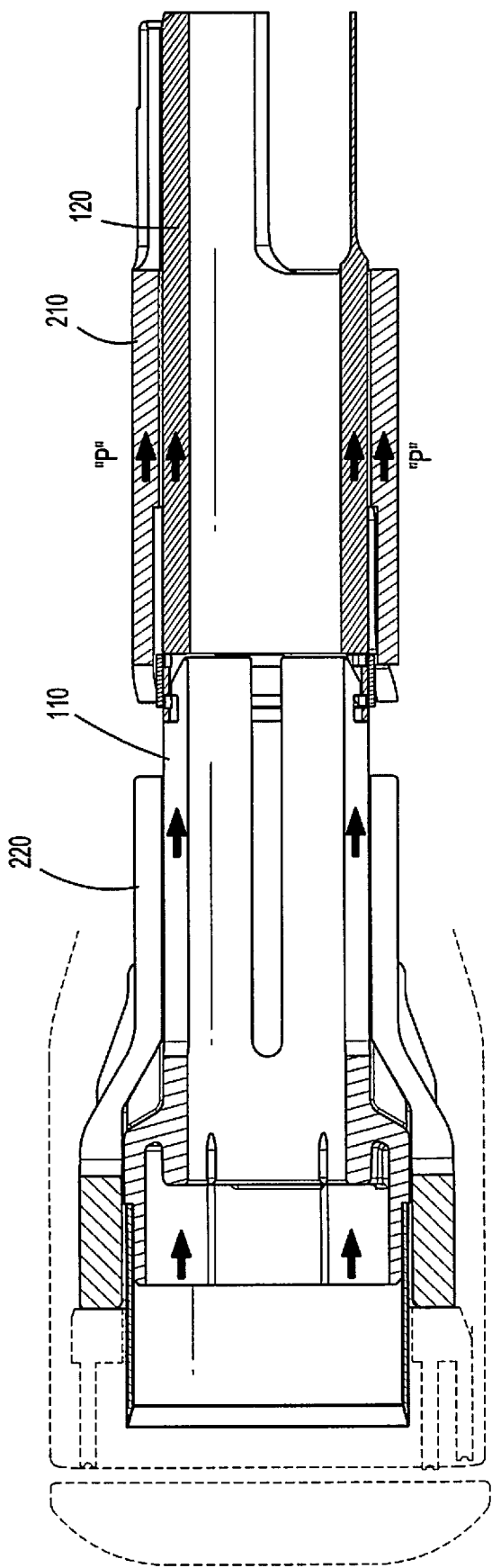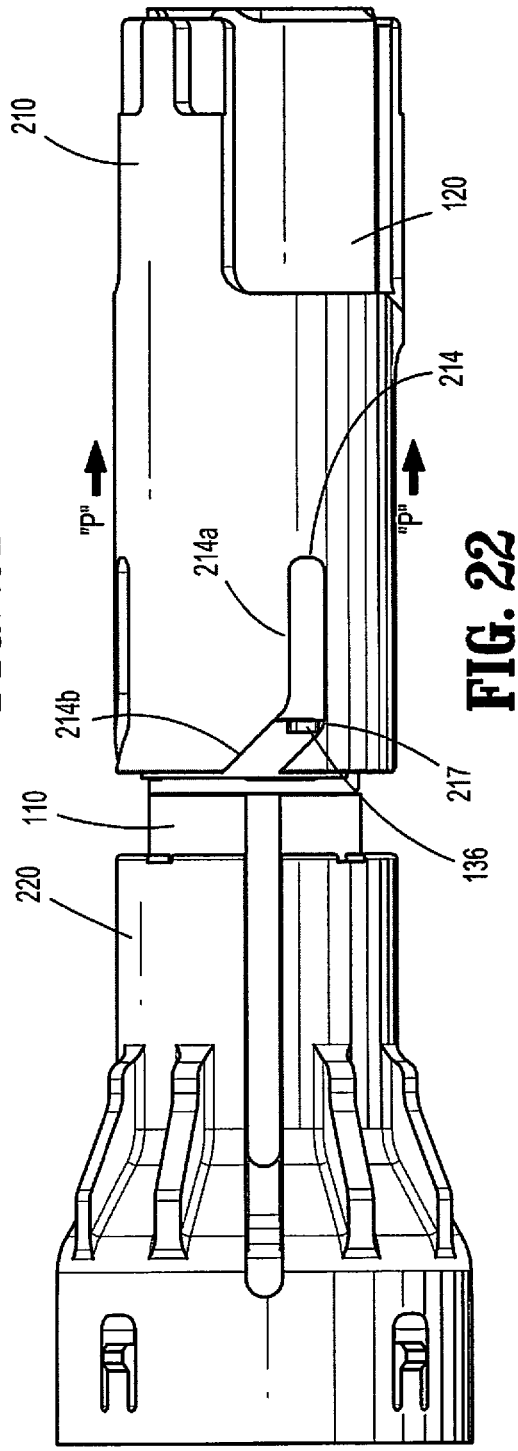

SNAP RING CAM ACTUATOR RELEASE FOR A LOADING UNIT

BACKGROUND

Technical Field

The present disclosure relates to surgical instruments, and more particularly, to detachable loading units that are releasably connectable to surgical instruments.

Background of Related Art

Surgical instruments for applying staples, clips, or other fasteners to tissue are well known. Typically, surgical instruments include an actuation unit, e.g., a handle assembly for actuating the instrument, an adapter assembly, and an end effector. Adapter assemblies have been developed for selective attachment to the handle assemblies and to a variety of end effectors. End effectors include a loading unit. Following use, the end effector may be disposed of along with the adapter. In some instances, the end effector and/or adapter assembly may be sterilized for reuse.

Accordingly, new reliable surgical instruments that enable easy and efficient attachment and removal of a loading unit would be desirable.

SUMMARY

The present disclosure describes detachable loading unit for use with a surgical instrument that demonstrate a practical approach to meeting the performance requirements and overcoming the usability challenges associated with loading unit attachment and removal. In general, the present disclosure describes a surgical instrument that includes a handle assembly, an adapter assembly extending from the handle assembly, and an elongate member operatively coupled with the handle assembly.

In accordance with an embodiment of the present disclosure, there is provided a surgical instrument including a shell assembly and an adapter. The shell assembly includes a shell housing, a plurality of staples, a staple pusher configured to eject the plurality of staples from the shell housing, a staple actuator configured to engage the staple pusher, a knife member, and a knife carrier supporting the knife member. The adapter includes a staple band operatively coupled to an actuation mechanism for axial displacement, a knife band at least partially received within the staple band, and a cam ring rotatably supported about the knife band. The staple band is configured to releasably engage the staple actuator. The knife band is operatively coupled with an actuation mechanism for axial displacement. The cam ring is rotatable between an engaged position in which the knife carrier engages the cam ring for concomitant axial displacement with the knife band and a disengaged position in which the knife carrier is disengaged from the cam ring.

In an embodiment, the cam ring may include an inner tab extending radially inward from an inner surface of the cam ring. The inner tab may be configured to engage the knife carrier.

In another embodiment, the knife carrier may include a finger including a groove configured to receive the inner tab of the cam ring.

In yet another embodiment, the knife band may define a slot configured to receive the inner tab such that the inner tab extends radially inward through the slot. In particular, the slot of the knife band may be dimensioned to enable rotation of the cam ring about the knife band, while inhibiting axial displacement of the cam ring relative to the knife band.

In still yet another embodiment, the knife carrier may define a longitudinal slot.

In still yet another embodiment, when the cam ring is in the engaged position the inner tab of the cam ring may extend radially inward through the slot of the knife band and engage the groove of the finger of the knife carrier, and when the cam ring is in the disengaged position the inner tab may be aligned with the longitudinal slot of the knife carrier.

In still yet another embodiment, the finger of the knife carrier may be configured to deflect radially inward.

In still yet another embodiment, the cam ring may include an outer tab extending radially outward.

In still yet another embodiment, the staple band may include a camming slot configured to slidably receive the outer tab of the cam ring.

In an embodiment, the staple band may define a longitudinal axis. The camming slot of the staple band may include a longitudinal portion extending along the longitudinal axis and an angled portion defining an acute angle with respect to the longitudinal axis.

In another embodiment, when the outer tab of the cam ring slides through the longitudinal portion of the camming slot of the staple band, the inner tab of the cam ring may engage the groove of the finger of the knife carrier such that axial displacement of the knife band causes concomitant axial displacement of the knife carrier.

In yet another embodiment, when the outer tab of the cam ring slides through the angled portion of the camming slot of the staple band, the cam ring may rotate about the knife band to position the inner tab in registration with the longitudinal slot of the knife carrier to detach the knife carrier and the staple actuator from the knife band and the staple band.

In accordance with another embodiment of the present disclosure, there is provided a surgical stapler including a handle assembly including an actuation mechanism, an adapter assembly operatively coupled with the handle assembly, an anvil assembly, and a shell assembly. The adapter assembly includes a staple band operatively coupled with the actuation mechanism for axial displacement, a knife band operatively coupled to the actuation mechanism for axial displacement, and a cam ring rotatably supported on the knife band. The knife band is at least partially received within the staple band. The shell assembly includes a plurality of staples, a staple pusher configured to eject the plurality of staples, a staple actuator configured for axial displacement to actuate the staple pusher, and a knife carrier supporting a knife member. The staple actuator is configured to engage the staple band. The cam ring is rotatable between an engaged position in which the knife carrier engages the cam ring for concomitant axial displacement with the knife band and a disengaged position in which the knife carrier is disengaged from the cam ring.

BRIEF DESCRIPTION OF THE DRAWINGS

The accompanying drawings illustrate exemplary embodiments of the disclosure and, together with a general description of the disclosure given above, and a detailed description of embodiments given below, serve to explain the principles of the disclosure, wherein:

FIG. 14 is an enlarged view of the indicated area of detail of FIG. 12 with a finger of the knife carrier engaged with the knife band and deflected outwardly;

FIG. 15 is a side cross-sectional view of the staple actuator, the knife carrier, and the drive bands of FIG. 4 with the knife carrier engaged with the knife band;

FIG. 16 is an enlarged view of the indicated area of detail of FIG. 15;

FIG. 17 is a side cross-sectional view of the staple actuator, the knife carrier, and the drive bands of FIG. 4 as the staple actuator is advanced to fire staples;

FIG. 18 is a side view of the staple actuator, the knife carrier, and the drive bands of FIG. 17;

FIG. 19 is a side cross-sectional view of the staple actuator, the knife carrier, and the drive bands of FIG. 4 with the knife carrier advanced to cut tissue;

FIG. 20 is a side view of the staple actuator, the knife carrier, and the drive bands of FIG. 19;

FIG. 21 is a side cross-sectional view of the staple actuator, the knife carrier, and the drive bands of FIG. 19 with the knife carrier retracted to a neutral position to initiate detachment of the knife carrier from the knife band;

FIG. 22 is a side view of the staple actuator, the knife carrier, and the drive bands of FIG. 21;

DETAILED DESCRIPTION

Figure 1A:
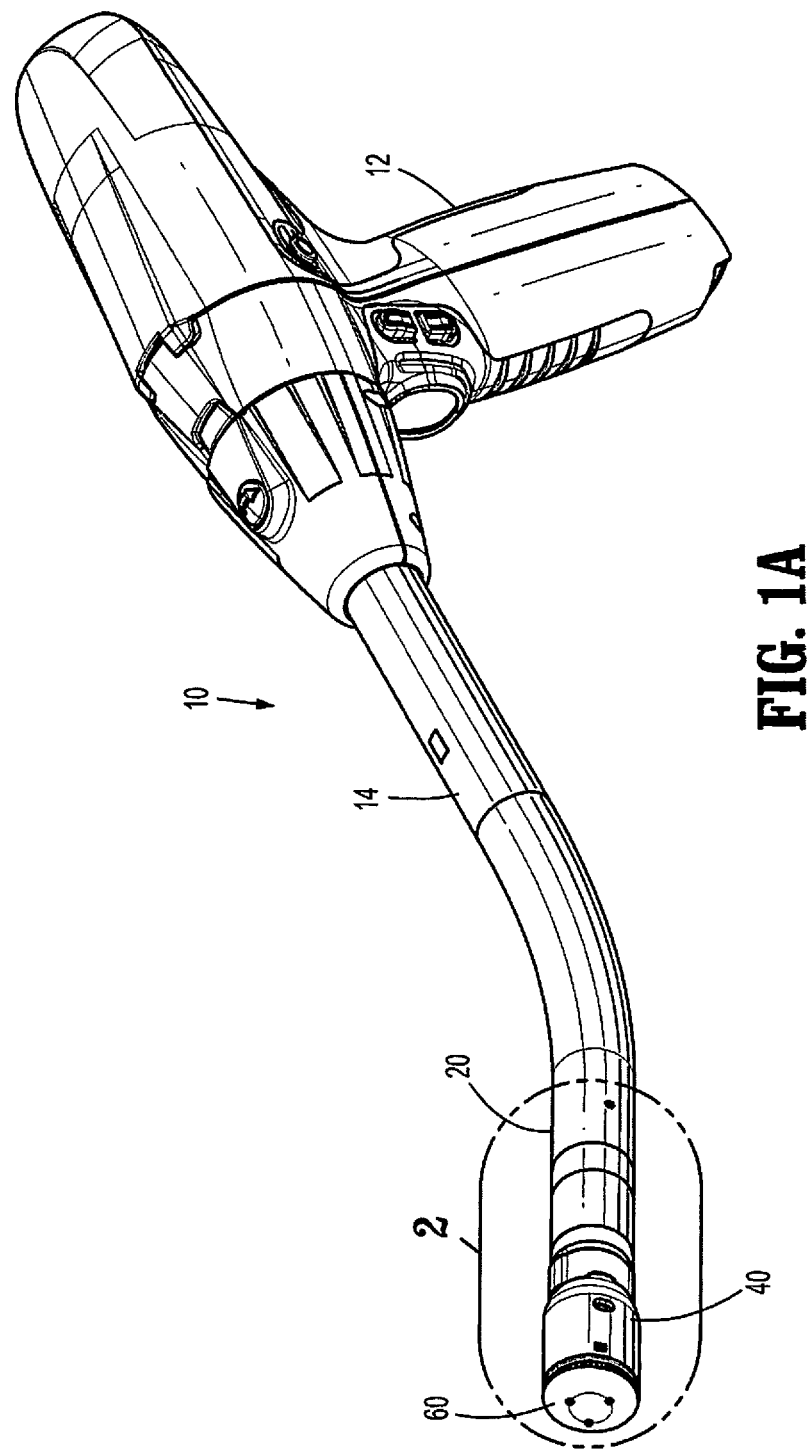
FIG. 1A is a perspective view of a surgical instrument including a detachable loading unit in accordance with an exemplary embodiment of the present disclosure.

Embodiments of the present disclosure are described in detail with reference to the drawings, in which like reference numerals designate identical or corresponding elements in each of the several views. As used herein, the term "distal" refers to that portion of an instrument that is farther from the user, while the term "proximal" refers to that portion of an instrument that is closer to the user.

The presently disclosed instrument includes a detachment mechanism that detachably connects a knife carrier and a staple actuator of a loading unit with a knife band and a staple band of an adapter assembly of a surgical stapler, respectively. The instrument demonstrates a practical approach to meeting the performance requirements and overcoming the usability challenges associated with attachment and removal of the knife carrier and the staple actuator with the knife band and the staple band, respectively. In particular, the detachment mechanism includes a staple actuator configured to engage a staple pusher, and a staple band operatively coupled to an actuation mechanism for axial displacement, a knife band at least partially received within the staple band, a cam ring rotatably supported about the knife band, and a knife carrier supporting a knife member. The knife band is operatively coupled with an actuation mechanism for axial displacement. The cam ring is rotatable between an engaged position in which the knife carrier engages the cam ring for concomitant axial displacement with the knife band and a disengaged position in which the knife carrier is disengaged from the cam ring.

Figure 1B:
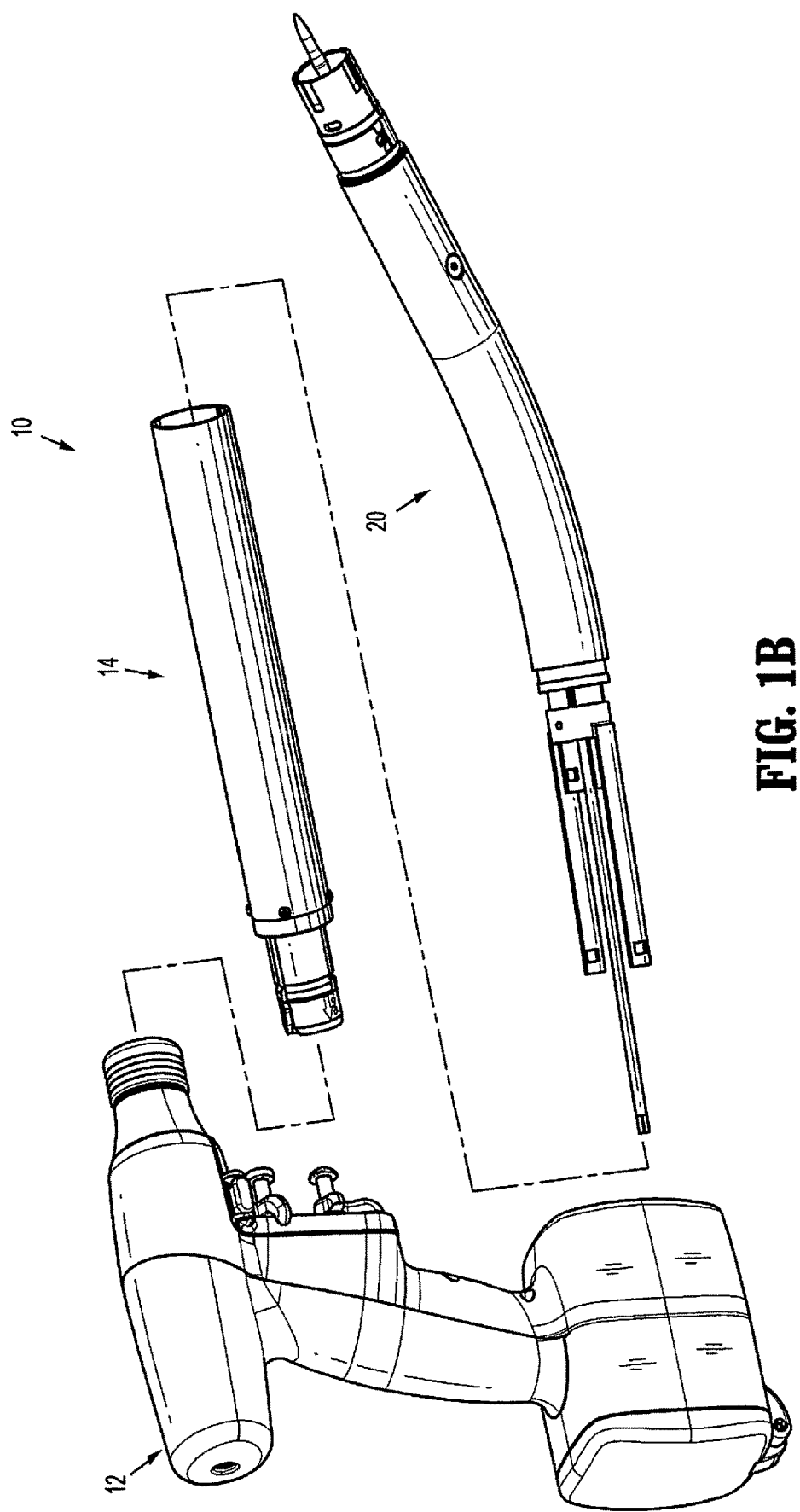
FIG. 1B is a perspective view of an adapter assembly and an extension member of the surgical instrument of FIG. 1A separated from a handle assembly of the surgical instrument.
Figure 1C:
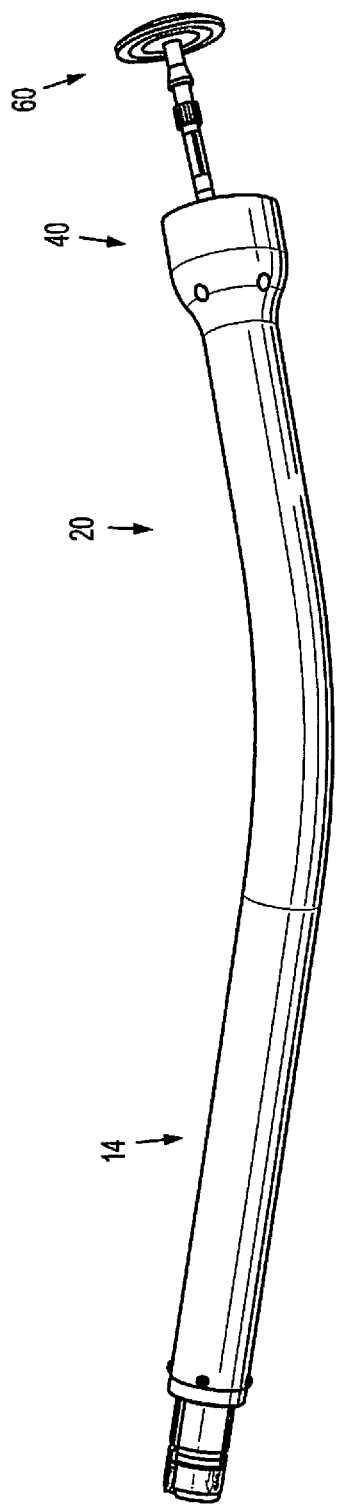
FIG. 1C is a perspective view of the adapter assembly and the extension member of FIG. 1B.

With reference to FIGS. 1A-1C, an exemplary embodiment of the present disclosure is generally shown as a surgical stapler 10. Surgical stapler 10 is adapted to be particularly useful in endoscopic or laparoscopic procedures, wherein an endoscopic portion of the surgical stapler 10 including a loading unit 40 and an anvil assembly 60 is insertable into an operative site through a small incision in a patient's body, a cannula assembly, or a natural body orifice (not shown). Surgical stapler 10 generally includes a handle assembly 12, an adapter assembly 14, and an extension assembly 20 which may be integrally formed with the adapter assembly 14. The adapter/extension assembly 14, 20 has a proximal end configured for selective connection to the handle assembly 12, and a distal end configured for operative connection to the loading unit 40. Reference may be made to U.S. Patent Application Publication No. 2012/0253329 and U.S. Patent Application Publication No. 2016/0106406 for a detailed discussion of the construction and operation of an exemplary electromechanically stapling instrument. The entire contents of each of these publications is incorporated herein by reference.

Figure 2:
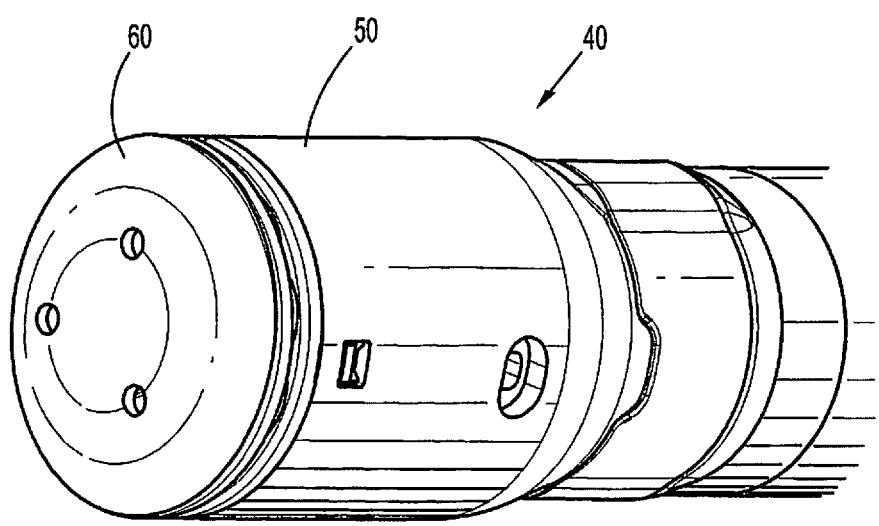
FIG. 2 is an enlarged view of the indicated area of detail of FIG. 1A.
Figure 3:
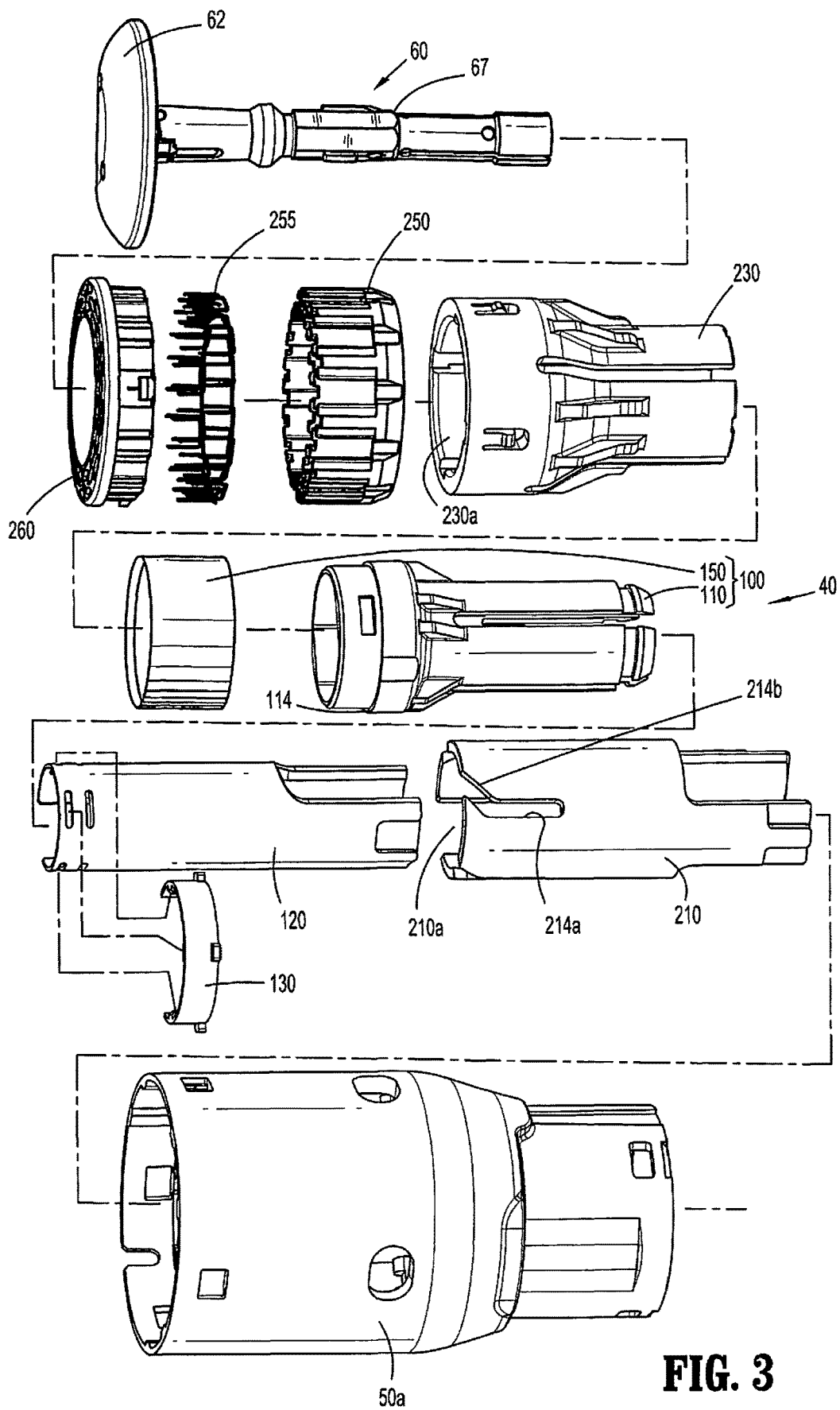
FIG. 3 is an exploded perspective view of the loading unit and drive bands of FIG. 1A with parts separated.
Figure 4:
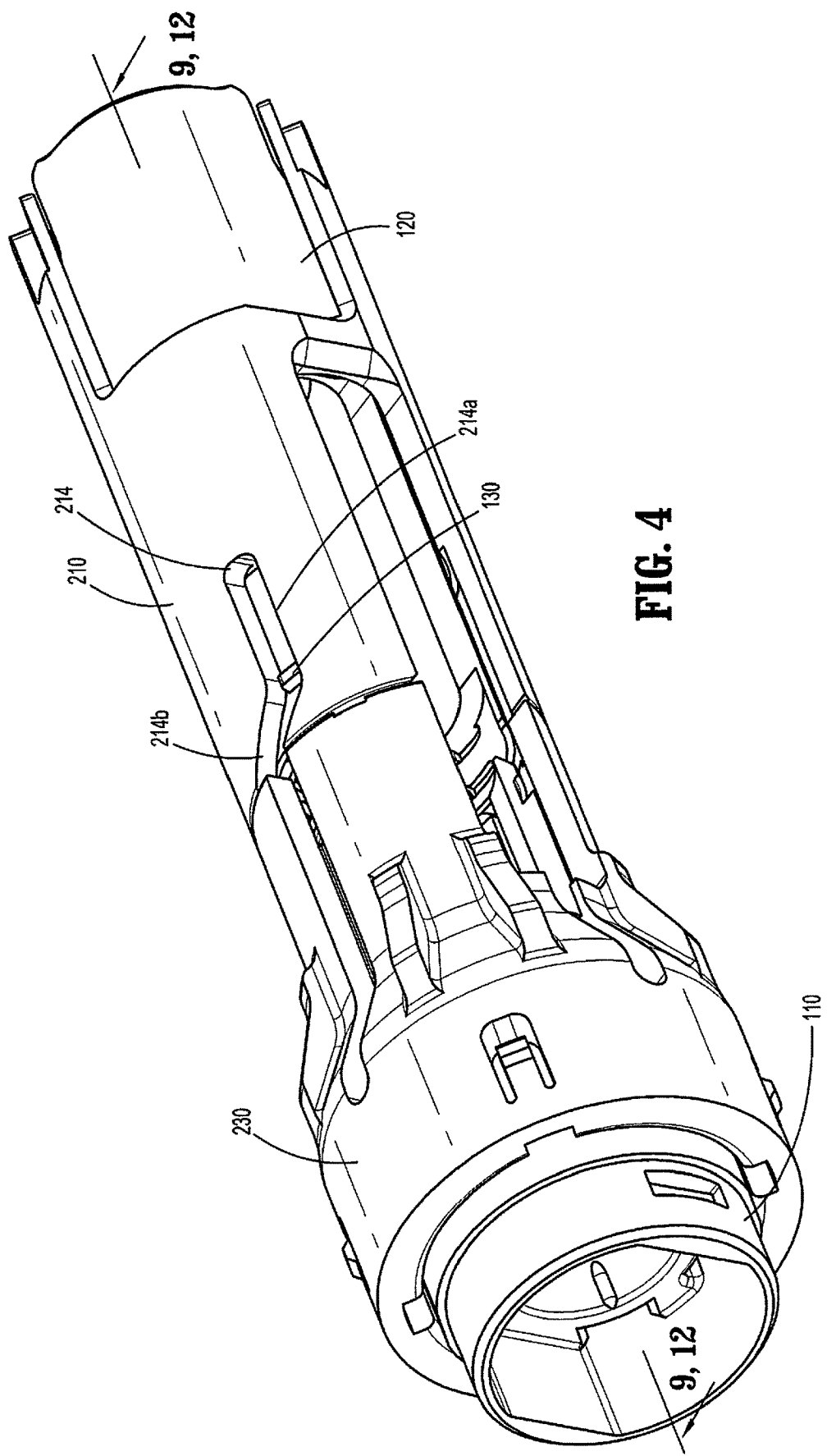
FIG. 4 is a perspective view of a staple actuator, a knife carrier, and the drive bands of FIG. 3.

With reference to FIGS. 2-4, the loading unit 40 includes a shell assembly 50 and the anvil assembly 60. The shell assembly 50 includes a shell housing 50a, a knife carrier 110 supporting a knife member 150, a staple actuator 230, a staple pusher 250, and a retaining member 260. The retaining member 260 defines an annular array of staple receiving slots 260a that receives staples 255. As described in further detail below, the staple actuator 230 is movable within the shell housing 50a to advance the staple pusher 250 partly through the retaining member 260 to eject the staples 255 from the retaining member 260. Similarly, the knife carrier 110 is movable within the shell housing 50a to advance the knife member 150 partly through the retaining member 260.

The adapter/extension assembly 14, 20 (FIG. 1C) includes a knife band 120 (FIG. 3) that is operatively coupled with knife carrier 110 and a staple band 210 (FIG. 3) that is operatively engaged with the staple actuator 230. Axial displacement of the knife band 120 causes concomitant axial displacement of knife carrier 110, which, in turn, advances the knife member 150 within the shell housing 50a. The staple actuator 230 is operatively associated with the staple band 210 such that axial displacement of the staple band 210 causes concomitant axial displacement of the staple actuator 230, which, in turn, causes the staple pusher 250 to eject the plurality of staples 255 from the annular array of slots of the retaining member 260.

The anvil assembly 60 includes an anvil member 62 and a stem 67 that extends from the anvil member 62. The stem 67 is operatively coupled to an approximation mechanism (not shown) in the adapter/extension assembly 14, 20 and the handle assembly 12 to provide axial displacement of stem 67 within the shell assembly 50 (FIG. 1) to transition the anvil member 62 in relation to the retaining member 260 of the shell assembly 50 between an approximated position in which anvil member 62 is disposed adjacent retaining member 260 and a spaced apart position in which anvil member 62 is spaced apart from retaining member 260 to receive tissue.

With reference to FIGS. 3 and 4, the knife band 120 is releasably coupled to the knife carrier 110. At least a portion of the knife assembly 100 is movably disposed within a channel 230a defined by the staple actuator 230 and a channel 210a defined by the staple band 210. The staple band 210 is operatively coupled with the knife band 120 to enable coupling and uncoupling of the knife band 120 and the knife carrier 110. When the knife carrier 110 is disengaged from the knife band 120, the staple actuator 230 disengages from the staple band 210.

Figure 5:
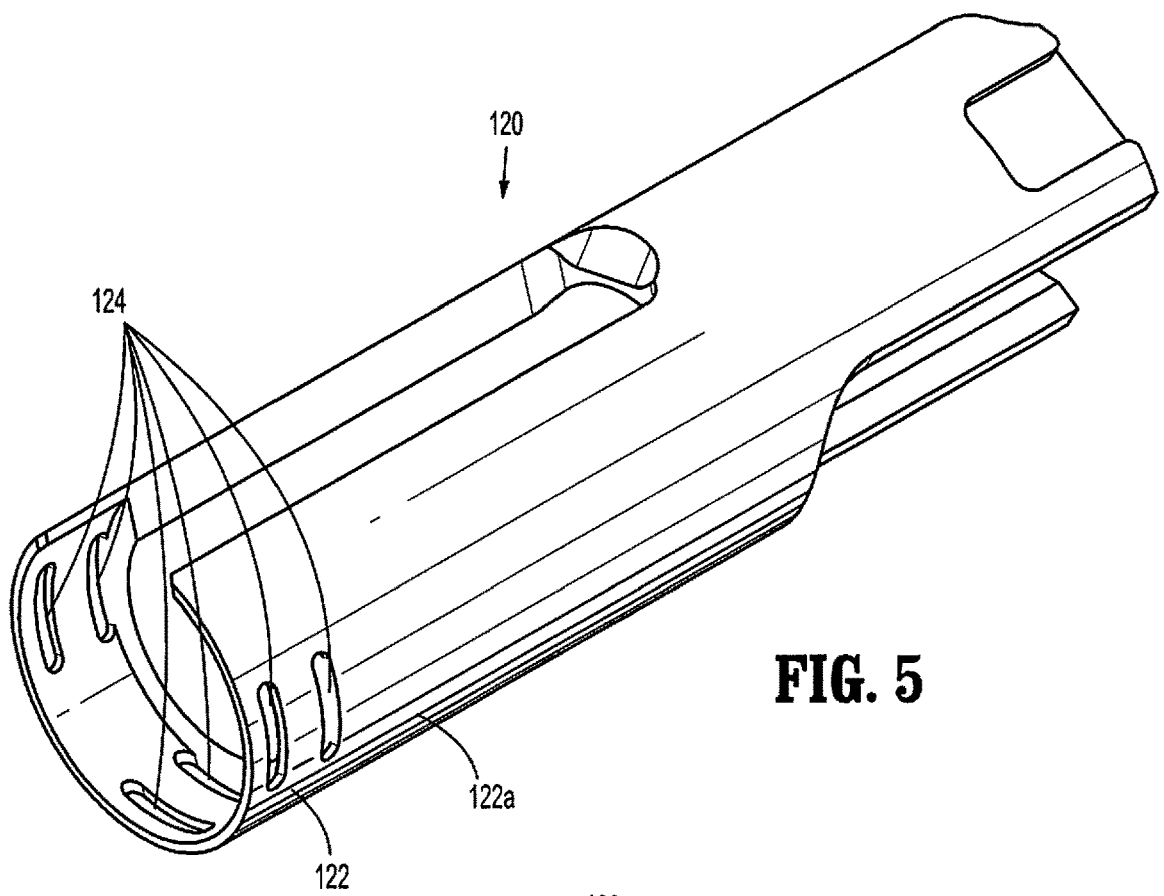
FIG. 5 is a perspective view of a knife band of FIG. 4.
Figure 6:
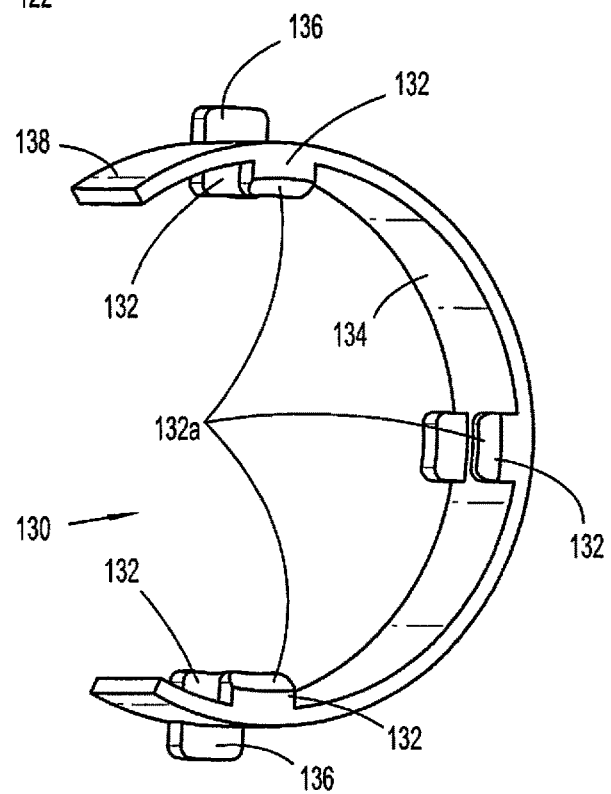
FIG. 6 is a perspective view of a cam ring that is operably engagable with the knife band of FIG. 4.
Figure 7:
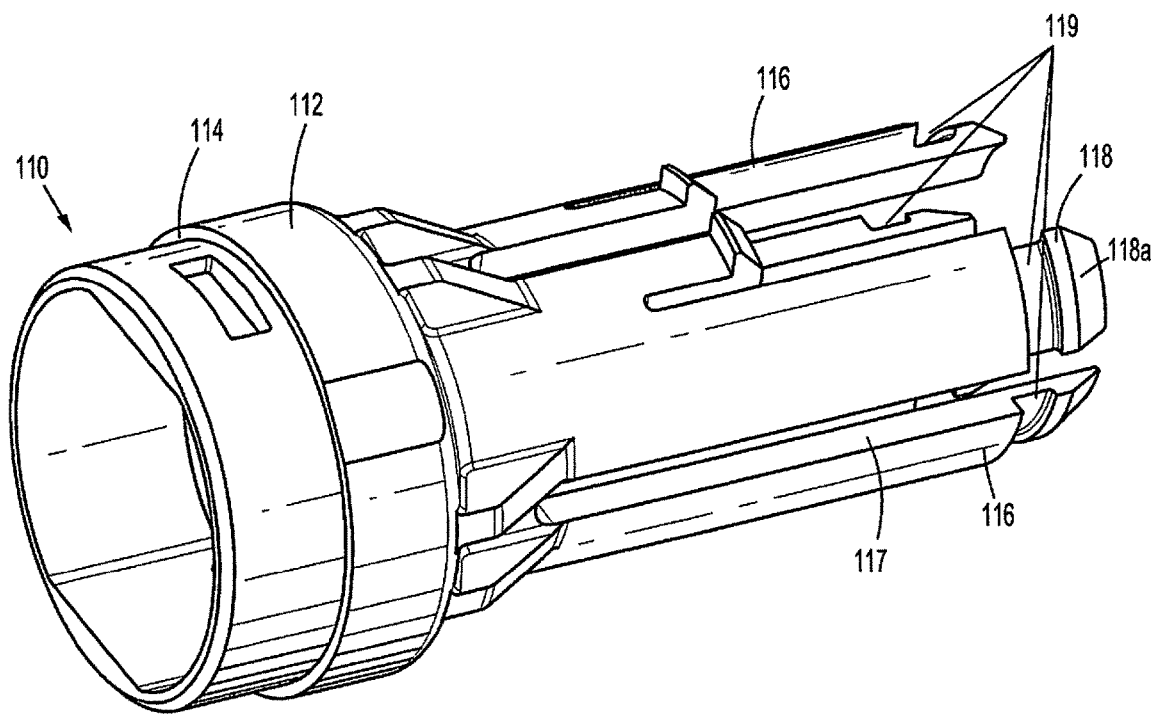
FIG. 7 is a perspective view of the knife carrier of FIG. 4.

With reference now to FIGS. 5-7, the knife carrier 110 is releasably coupled to the knife band 120. To this end, the knife band 120 supports a cam ring 130 that includes inner tabs 132, an inner surface 134, outer tabs 136, and an outer surface 138. The inner tabs 132 extend radially inward from the inner surface 134 of the cam ring 130 and the outer tabs 136 extend radially outward from the outer surface 138 of the cam ring 130. The inner surface 134 of the cam ring 130 engages an outer surface 122a of a distal portion 122 of the knife band 120 such that the inner tabs 132 extend radially inward through respective camming slots 124 defined in the distal portion 122 of the knife band 120. The camming slots 124 have a length that is greater than the length of the inner tabs 132 such that the cam ring 130 is rotatable to a limited extent about the outer surface 122a of the knife band 120. However, the width of the camming slots 124 is substantially equal to the width of the inner tabs 132 to substantially inhibit relative axial displacement between the knife band 120 and the cam ring 130. The inner tabs 132 extend through the respective camming slots 124 of the knife band 120 into engagement with the knife carrier 110 to releasably secure the knife band 120 to the knife carrier 110, as will be discussed hereinbelow.

With particular reference now to FIG. 7, the knife carrier 110 includes a head portion 112 having a support 114 that is configured to retain knife member 150 (FIG. 3) to the knife carrier 110. In embodiments, the support 114 includes a cylindrical stepped portion 114 that receives the knife member 150. The knife carrier 110 further includes resilient fingers 116 that extend proximally from the head portion 112. At least a portion of each of the fingers 116 is received within knife band 120 when the knife band 120 is coupled to the knife carrier 120. Each of the fingers 116 is radially flexible. Adjacent fingers 116 define a longitudinal slot 117 that is configured to receive a respective one of the inner tabs 132 of the cam ring 130. Each of the fingers 116 includes a proximal portion 118 that defines a groove 119 that is dimensioned to receive the respective inner tab 132 of the cam ring 130 that extends radially inward through the camming slots 124 of the knife band 120.

Figures 9, 10:
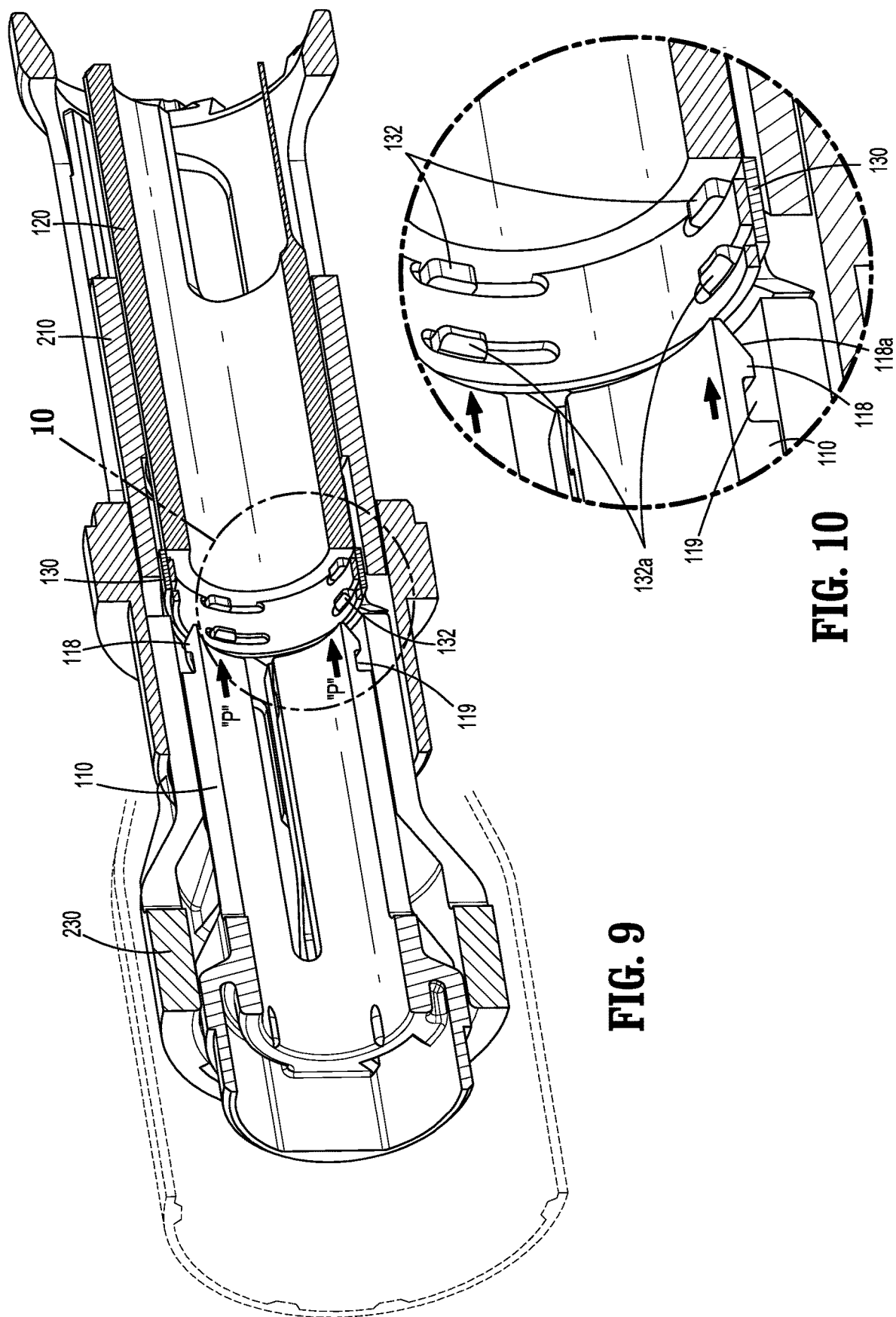
FIG. 9 is a perspective view of the staple actuator, the knife carrier, and the drive bands taken along section line 9-9 of FIG. 4.
FIG. 10 is an enlarged view of the indicated area of detail of FIG. 9.

With reference to FIGS. 9 and 10, in order to couple the knife carrier 110 with the cam ring 130, the cam ring 130 is positioned about the outer surface 122a of a distal portion 122 of the knife band 120 such that the inner tabs 132 of the cam ring 130 extend through the camming slots 124. Thereafter, the proximal portion 118 of the knife carrier 110 is placed within the knife band 120 such that the grooves 119 of the knife carrier 110 receive the respective inner tabs 132 of cam ring 130. At least some of the inner tabs 132 of the cam ring 130 may include chamfered portions 132a and the proximal portion 118 of the knife carrier 110 may include chamfered portions 118a to facilitate positioning of the inner tabs 132 within the respective grooves 119. More specifically, when the distal portion 118 of the knife carrier 110 is pushed in the direction of arrow "P" in FIG. 9 into the cam ring 130, the chamfered surfaces 132a of the inner tabs 132 will engage the chamfered surfaces 118a of the knife carrier 118 to smoothly urge the inner tabs 132 into the grooves 119.

Figure 8:
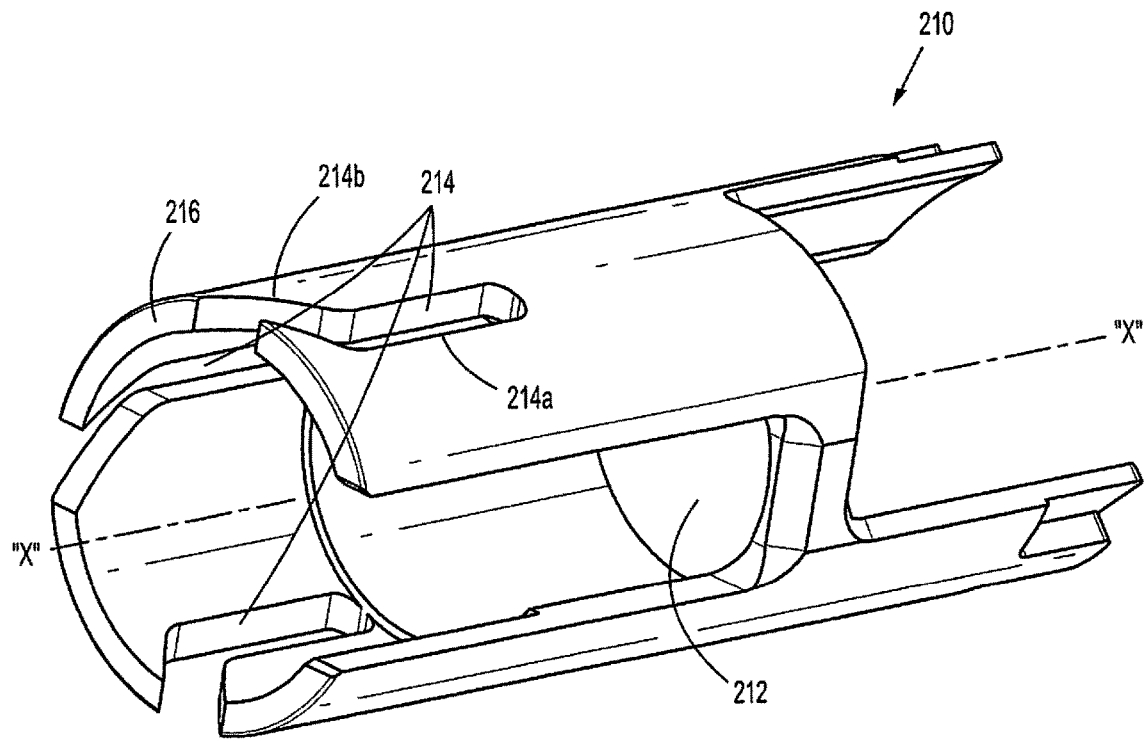
FIG. 8 is a perspective view of the staple band of FIG. 4.

With reference back to FIGS. 3 and 8, the staple band 210 defines the channel 210a that is configured to receive at least a portion of the knife band 120 and the knife carrier 110 for movement between retracted and advanced positions. The staple band 210 is configured to engage the staple actuator 230 to move the staple actuator 230 towards an advanced position. In particular, the staple band 210 includes a distal portion 216 that is configured to engage the staple actuator 230 such that distal axial displacement of the staple band 210 from the retracted position to the advanced position causes distal axial displacement of the staple actuator 230. The staple band 210 defines cam slots 214 that are dimensioned to receive the respective outer tabs 136 (FIG. 6) of the cam ring 130 (FIG. 5). Each of the cam slots 214 includes a longitudinal portion 214a that extends along an axis that is parallel to a longitudinal axis "X-X" of the staple band 210 and an angled portion 214b that defines an acute angle with respect to the longitudinal axis "X-X" of staple band 210.

Figure 11:
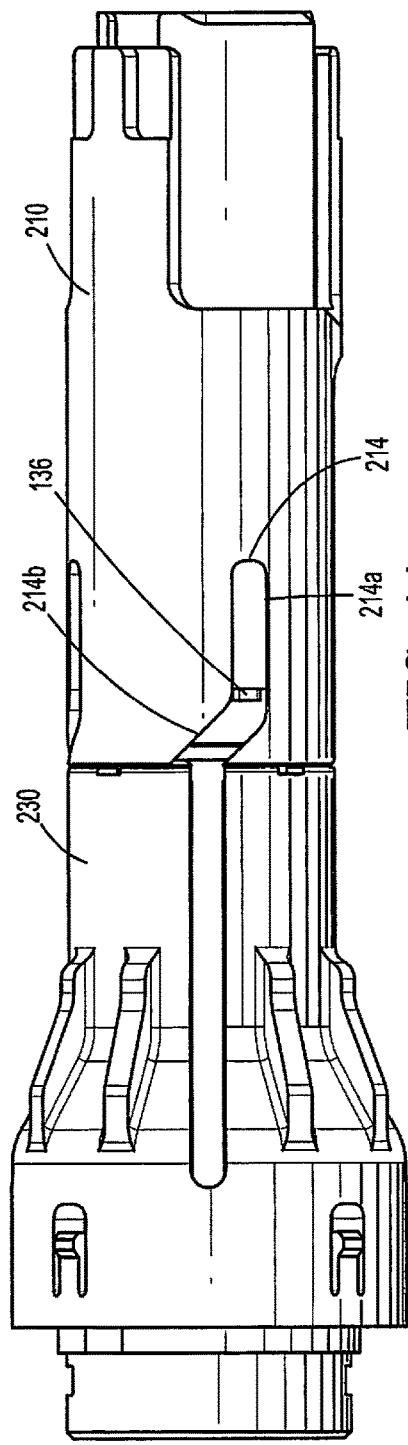
FIG. 11 is a side view of the staple actuator, the knife carrier, and the drive bands of FIG. 4.
Figure 12:
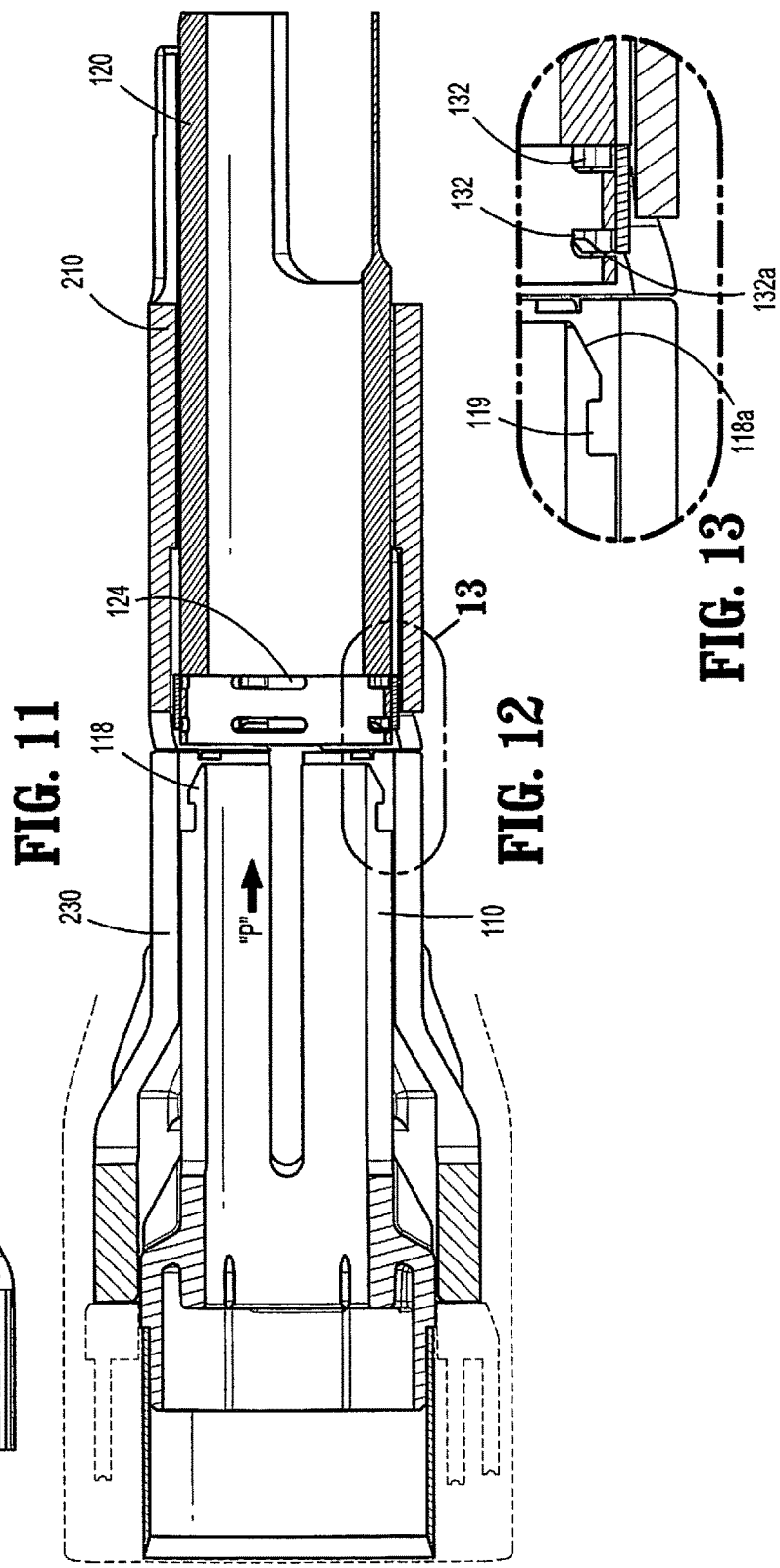
FIG. 12 is a side cross-sectional view of the staple actuator, the knife carrier, and the drive bands taken along section line 12-12 of FIG. 4.
Figure 13:
FIG. 13 is an enlarged view of the indicated area of detail of FIG. 12.

With reference now to FIGS. 11-13, initially, a proximal end of the staple actuator 230 is engaged with a distal end of the staple band 210, and the knife carrier 110 is disposed within the channel 230a of the staple actuator 230 and is detached from the knife band 120. As discussed above, the knife band 120 and the staple band 210 are coupled to mechanisms within the adapter/extension assembly 14, 20 and the handle assembly 12 (FIG. 1) such that the knife band 120 and the staple band 210 are movable in relation to the shell housing 50a.

With reference now to FIGS. 14-16, in order to operatively couple the knife carrier 110 with the knife band 120, the proximal portion 118 of the knife carrier 110 is received within the knife band 120 such that the grooves 119 of the knife carrier 110 engage the respective inner tabs 132 of the cam ring 130 to position the inner tabs 132 within the grooves 119. More specifically, when the knife carrier 110 is moved proximally in the direction of arrow "P" in FIG. 12, the chamfered portion 118a (FIG. 7) of each of the fingers 116 of the knife carrier 110 and the chamfered portion 132a of each of the inner tabs 132 of the cam ring 130 engage to deflect the fingers 116 inwardly and direct the inner tabs 132 of the cam ring 130 into the respective grooves 119 of the fingers 116. While the inner tabs 132 of the cam ring 130 extend through the camming slots 124 of the knife band 120 and are received within the grooves 119 of the fingers 116 of the knife carrier 110, the outer tabs 136 (FIG. 11) of the cam ring 130 are slidably received within the cam slots 214 of the staple band 210. Once the inner tabs 132 of the cam ring 130 are received in the respective grooves 119, axial movement of the knife band 120 will cause axial movement of the knife carrier 110.

With reference now to FIGS. 17 and 18, in use, the staple band 210 is displaced distally (in the direction of arrow "D" in FIG. 17) to advance the staple actuator 230 within the shell housing 50a of the shell assembly 50. Advancement of the staple actuator 230 within the shell housing 50a causes staple pusher 250 (FIG. 3) to move at least partially through the retaining member 260 to eject the staples 255 from the retaining member 260. As the staple band 210 is advanced within the shell housing 50a, the outer tabs 136 of the cam ring 130 which is supported on the knife band 120 and is stationary translates through the longitudinal portions 214a of the cam slots 214 of the staple band 210. This enables the staple band 210 to move axially independently of the knife band 120 within the shell housing 50a. In this manner, the angular orientation of the cam ring 130 is unaffected by initial axial advancement of the staple band 210 in relation to the shell housing 50a. Thus, the knife carrier 110 remains engaged with knife band 120 during advancement of the staple band 210 and the staple actuator 230. As illustrated in FIG. 18, advancement of the staple actuator 230 to eject the staples 255 from the retaining member 260 repositions each of the outer tabs 136 of the cam ring 130 towards a respective proximal-most portion 215 of the cam slot 214. In this manner, the staple actuator 230 may be actuated independently of the knife carrier 110 and/or knife band 120.

With reference now to FIGS. 19 and 20, the knife carrier 110 is operatively coupled with the knife band 120 such that axial displacement of the knife band 120 in the direction of arrow "D" in FIG. 19 causes axial displacement of the knife carrier 110 in the direction of arrow "D", which, in turn, advances the knife member 150 (FIG. 3) within the shell housing 50a. Advancement of the knife band 120 moves each of the outer tabs 136 of the cam ring 130 towards a respective distal-most portion 217 of the longitudinal portion 214a of the cam slot 214. In this manner, the knife member 150 is advanced independently of the staple actuator 230 and the staple band 210. As discussed above, the knife member 150 is advanced through the retaining member 260 to dissect tissue disposed radially inwardly of the annular array of staples 255 ejected from the retaining member 260.

Figure 23:
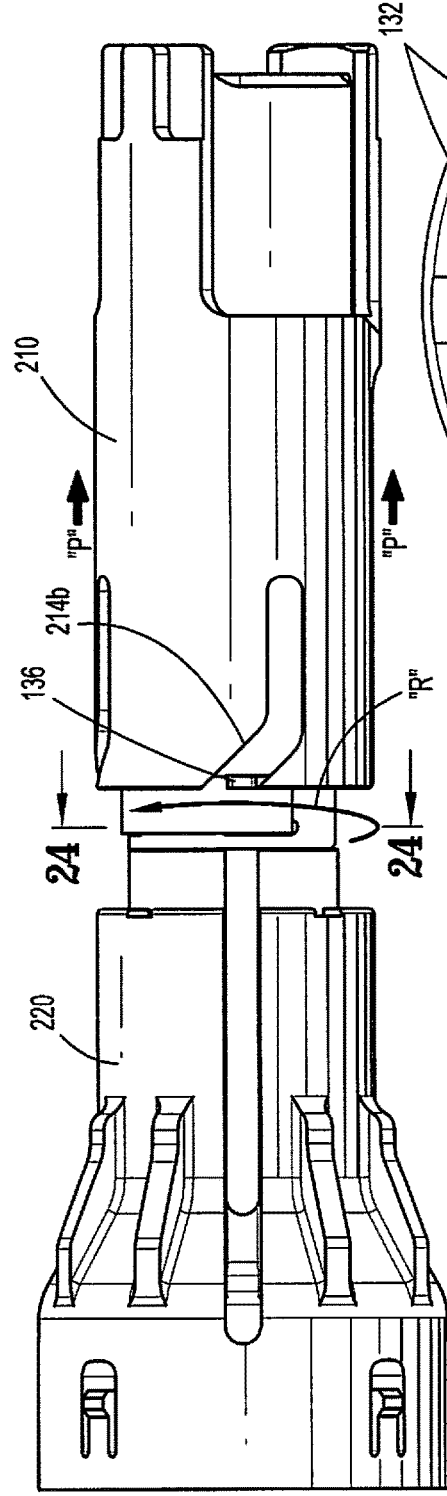
FIG. 23 is a side view of the portion of the staple actuator, the knife carrier, and the drive bands of FIG. 22 with a cam ring rotated to disengage the staple actuator and the knife carrier from the staple band and the knife band.
Figure 24:
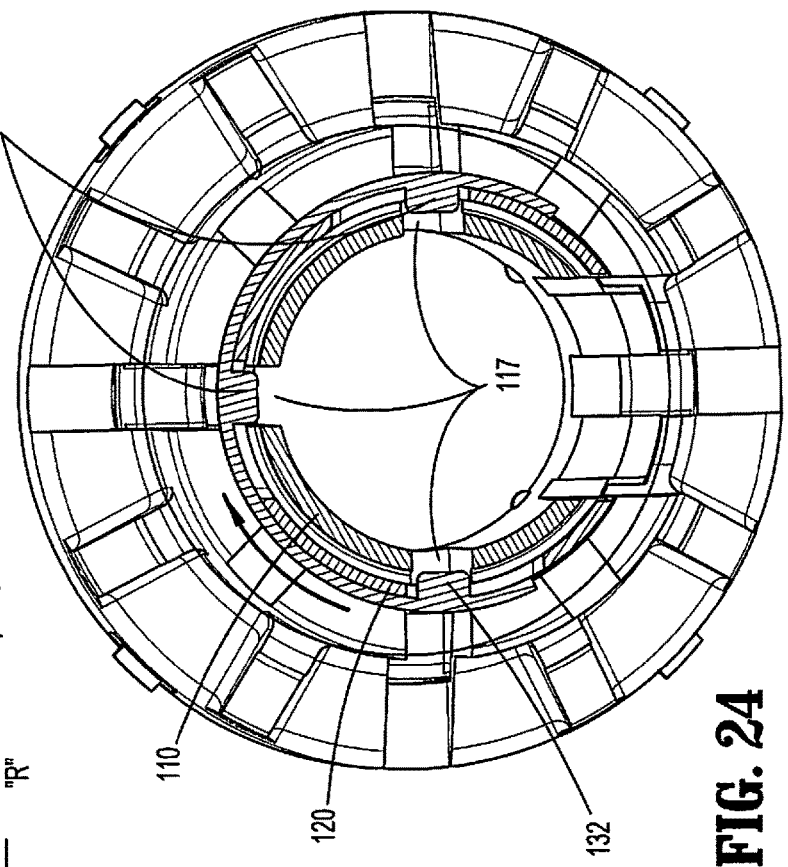
FIG. 24 is a cross-sectional view of the staple actuator, the knife carrier, and the drive bands of FIG. 23 illustrating rotation of the cam ring.

With reference now to FIGS. 21-24, the knife carrier 110 may be detached from the knife band 120 by retracting the knife band 120 in relation to the staple band 210. Initially, after the staples 255 are ejected from the retaining member 260 and the knife member 150 is advanced to dissect tissue, the staple band 210 and the knife band 120 can be retracted together or separately in the direction of arrow "P" in FIGS. 21 and 22 to a neutral position. In the neutral position, the outer tabs 136 of the cam ring 130 are positioned in respective longitudinal portions 214a of cam slots 214. After the staple band 210 and the knife band 210 reach the neutral position, the knife band 120 and the knife carrier 110 are moved independently of the staple band 120 in the direction of arrow "P" to move the outer tabs 136 of the cam ring 130 through the respective angled portions 214b of the cam slots 214 of the staple band 210. When the outer tabs 136 slide along the respective angled portions 214b, engagement of the outer tabs 136 with the walls defining the cam slots 214 causes the cam ring 130 to rotate in the direction of arrow "R" as indicated in FIG. 23. The cam ring 130 is able to rotate about the distal portion of the knife band 120 because as discussed above the circumferential dimension or length of each of the camming slots 124 (FIG. 5) is larger than the length of the inner tabs 136 of the cam ring 130. Thus, the inner tabs 132 of the cam ring 130 slide within the respective camming slots 124 of the knife band 120 causing rotation of the cam ring 130 about the outer surface 122a of the knife band 120. As the cam ring 130 rotates about the knife band 120, the inner tabs 132 align with the respective longitudinal slots 117 of the knife carrier 110. With particular reference to FIG. 24, in this manner, the staple band 210 rotates the cam ring 130 out of engagement with the knife carrier 110 as the knife band 120 is retracted to a fully retracted position. At this time, the knife carrier 110 and the staple actuator 230 are detached from the knife band 120 and the staple band 210, respectively. Under such a configuration, the relative movement between the staple actuator 230 and the staple band 210 and the knife carrier 110 and the knife band 120 during the detachment process is minimized.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical instrument comprising:
   a shell assembly including:
      a shell housing;
      a plurality of staples;
      a staple pusher configured to eject the plurality of staples from the shell housing;
      a staple actuator configured to engage the staple pusher;
      a knife member; and
      a knife carrier supporting the knife member, the knife carrier including a finger defining a groove; and
   an adapter including:
      a staple band operatively coupled to a first actuation mechanism for axial displacement, the staple band configured to releasably engage the staple actuator; and
      a knife band at least partially received within the staple band, the knife band defining a slot, the knife band operatively coupled with a second actuation mechanism for axial displacement; and
      a cam ring rotatably supported about the knife band, the cam ring including an inner tab extending radially inward from an inner surface of the cam ring, the inner tab configured to engage the groove of the knife carrier and the slot of the knife band such that the inner tab extends radially inward through the slot, the cam ring being rotatable between an engaged position in which the knife carrier engages the cam ring for concomitant axial displacement with the knife band and a disengaged position in which the knife carrier is disengaged from the cam ring.

2. The surgical instrument according to claim 1, wherein the slot of the knife band is dimensioned to enable rotation of the cam ring about the knife band, while inhibiting axial displacement of the cam ring relative to the knife band.

3. The surgical instrument according to claim 2, wherein the knife carrier defines a longitudinal slot.

4. The surgical instrument according to claim 3, wherein when the cam ring is in the engaged position the inner tab of the cam ring extends radially inward through the slot of the knife band and engages the groove of the finger of the knife carrier, and when the cam ring is in the disengaged position the inner tab is aligned with the longitudinal slot of the knife carrier.

5. The surgical instrument according to claim 1, wherein the finger of the knife carrier is configured to deflect radially inward.

6. The surgical instrument according to claim 3, wherein the cam ring includes an outer tab extending radially outward.

7. The surgical instrument according to claim 6, wherein the staple band includes a camming slot configured to slidably receive the outer tab of the cam ring.

8. The surgical instrument according to claim 7, wherein the staple band defines a longitudinal axis, the camming slot of the staple band including a longitudinal portion extending along the longitudinal axis and an angled portion defining an acute angle with respect to the longitudinal axis.

9. The surgical instrument according to claim 8, wherein when the outer tab of the cam ring slides through the longitudinal portion of the camming slot of the staple band, the inner tab of the cam ring engages the groove of the finger of the knife carrier such that axial displacement of the knife band causes concomitant axial displacement of the knife carrier.

10. The surgical instrument according to claim 8, wherein when the outer tab of the cam ring slides through the angled portion of the camming slot of the staple band, the cam ring rotates about the knife band to position the inner tab in registration with the longitudinal slot of the knife carrier to detach the knife carrier and the staple actuator from the knife band and the staple band.

11. A surgical stapler comprising:
    a handle assembly including first and second actuation mechanisms;
    an adapter assembly operatively coupled with the handle assembly, the adapter assembly including:
        a staple band operatively coupled with the first actuation mechanism for axial displacement; and
        a knife band at least partially received within the staple band, the knife band defining a slot, the knife band operatively coupled to the second actuation mechanism for axial displacement; and
    a cam ring rotatably supported on the knife band, the cam ring includes an inner tab configured to extend radially inward through the slot of the knife band from an inner surface of the cam ring;
    an anvil assembly; and
    a shell assembly including:
        a plurality of staples;
        a staple pusher configured to eject the plurality of staples;
        a staple actuator configured for axial displacement to actuate the staple pusher, the staple actuator configured to engage the staple band; and
        a knife carrier supporting a knife member, the cam ring rotatable between an engaged position in which the knife carrier engages the cam ring for concomitant axial displacement with the knife band and a disengaged position in which the knife carrier is disengaged from the cam ring, the knife carrier including a finger defining a groove configured to receive the inner tab of the cam ring when the cam ring is in the engaged position.

12. The surgical stapler according to claim 11, wherein the knife carrier defines a longitudinal slot, such that when the cam ring is in the disengaged position, the inner tab is aligned with the longitudinal slot of the knife carrier.

13. The surgical stapler according to claim 12, wherein the cam ring includes an outer tab extending radially outward, and the staple band includes a camming slot configured to receive the outer tab of the cam ring.

14. The surgical stapler according to claim 13, wherein the staple band defines a longitudinal axis, the camming slot of the staple band including a longitudinal portion extending along the longitudinal axis and an angled portion defining an acute angle with respect to the longitudinal axis, wherein when the outer tab of the cam ring slides through the longitudinal portion of the camming slot of the staple band, the inner tab of the cam ring engages the groove of the knife carrier such that axial displacement of the knife band causes concomitant axial displacement of the knife carrier.

15. The surgical stapler according to claim 14, wherein when the outer tab of the cam ring slides through the angled portion of the camming slot of the staple band, the cam ring partially rotates to place the inner tab in registration with the longitudinal slot of the knife carrier such that the knife carrier and the staple actuator are detachable from the staple band and the knife band.

* * * * *